(12) United States Patent
Wittens

(10) Patent No.: US 7,811,315 B2
(45) Date of Patent: Oct. 12, 2010

(54) IMPLANT VALVE FOR IMPLANTATION IN A BLOOD VESSEL

(76) Inventor: Cornelis Hendrikus Anna Wittens, K. van Tollaan 6, 3065 DA Rotterdam (NL)

( * ) Notice: Subject to any disclaimer, the term of this patent is extended or adjusted under 35 U.S.C. 154(b) by 1370 days.

(21) Appl. No.: 10/181,703

(22) PCT Filed: Jan. 16, 2001

(86) PCT No.: PCT/NL01/00027
§ 371 (c)(1),
(2), (4) Date: Oct. 24, 2002

(87) PCT Pub. No.: WO01/52775
PCT Pub. Date: Jul. 26, 2001

(65) Prior Publication Data
US 2003/0060875 A1   Mar. 27, 2003

(30) Foreign Application Priority Data
Jan. 17, 2000   (NL) .................................. 1014095

(51) Int. Cl.
*A61F 2/06* (2006.01)
(52) U.S. Cl. .................. 623/1.24; 623/1.26; 623/901; 623/2.18; 600/36
(58) Field of Classification Search ....... 623/1.23–1.32, 623/2.1–2.18, 901; 600/36
See application file for complete search history.

(56) References Cited
U.S. PATENT DOCUMENTS

| 4,214,587 | A | * | 7/1980 | Sakura, Jr. .................. 606/155 |
| 4,265,694 | A | * | 5/1981 | Boretos et al. ............... 156/242 |
| 4,470,157 | A | * | 9/1984 | Love .......................... 623/2.15 |
| 4,490,859 | A | * | 1/1985 | Black et al. ................. 623/2.16 |
| 4,638,544 | A | * | 1/1987 | McNeil ........................ 29/434 |
| 4,759,758 | A | * | 7/1988 | Gabbay ...................... 623/2.13 |
| 5,411,552 | A | * | 5/1995 | Andersen et al. ............ 623/2.18 |
| 5,489,295 | A | * | 2/1996 | Piplani et al. ............... 623/1.35 |
| 5,522,885 | A | * | 6/1996 | Love et al. .................. 623/2.11 |
| 5,562,726 | A | * | 10/1996 | Chuter ....................... 623/1.35 |
| 5,571,170 | A | * | 11/1996 | Palmaz et al. ............... 623/1.11 |
| 5,578,017 | A | * | 11/1996 | Aguilar et al. ............... 604/275 |
| 5,723,003 | A | * | 3/1998 | Winston et al. ............. 623/1.13 |
| 5,755,782 | A | * | 5/1998 | Love et al. .................. 623/1.15 |

(Continued)

FOREIGN PATENT DOCUMENTS

EP   0850 607   7/1998

*Primary Examiner*—Paul Prebilic
(74) *Attorney, Agent, or Firm*—Kinney & Lange, P.A.

(57) ABSTRACT

An implant valve for implantation in a blood vessel is comprised of a flexible tube and a hollow, substantially cylindrical support with a casing, expandable in diameter from an initial position to an implantation position. The support extends substantially coaxially over a part of the length of the tube along the inner wall of the tube. The casing of the support cooperates with the inner wall of the tube such that, in the implantation position, a first part of the tube can be formed into a rigid shell, which can be clamped substantially coaxially along the inner wall of a blood vessel. A second, axially contiguous part of the tube can then form a flexible, tubular valve body, which can extend substantially clear in the blood vessel. In an advantageous embodiment, the flexible tube comprises a vein turned inside out and the ends of the tube are connected to form a ring embracing the support.

8 Claims, 3 Drawing Sheets

U.S. PATENT DOCUMENTS

| | | | |
|---|---|---|---|
| 5,769,887 A * | 6/1998 | Brown et al. | 623/1.23 |
| 5,824,037 A * | 10/1998 | Fogarty et al. | 623/1.13 |
| 5,843,158 A * | 12/1998 | Lenker et al. | 623/1.13 |
| 5,851,232 A | 12/1998 | Lois | |
| 5,855,601 A | 1/1999 | Chuter et al. | |
| 5,906,641 A * | 5/1999 | Thompson et al. | 623/1.15 |
| 6,010,531 A * | 1/2000 | Donlon et al. | 623/2.1 |
| 6,036,723 A * | 3/2000 | Anidjar et al. | 623/1.13 |
| 6,117,166 A * | 9/2000 | Winston et al. | 623/1.13 |
| 6,126,686 A * | 10/2000 | Badylak et al. | 623/1.24 |
| 7,081,129 B2 * | 7/2006 | Chobotov | 623/1.13 |
| 2001/0021872 A1 * | 9/2001 | Bailey et al. | 623/1.24 |
| 2001/0032013 A1 * | 10/2001 | Marton | 623/1.15 |
| 2002/0111665 A1 * | 8/2002 | Lauterjung | 623/1.1 |
| 2002/0198594 A1 * | 12/2002 | Schreck | 623/2.11 |

\* cited by examiner

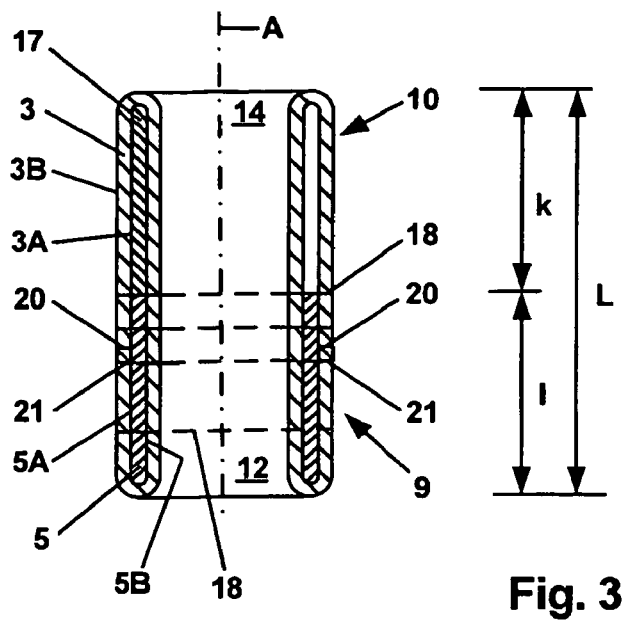
Fig. 3
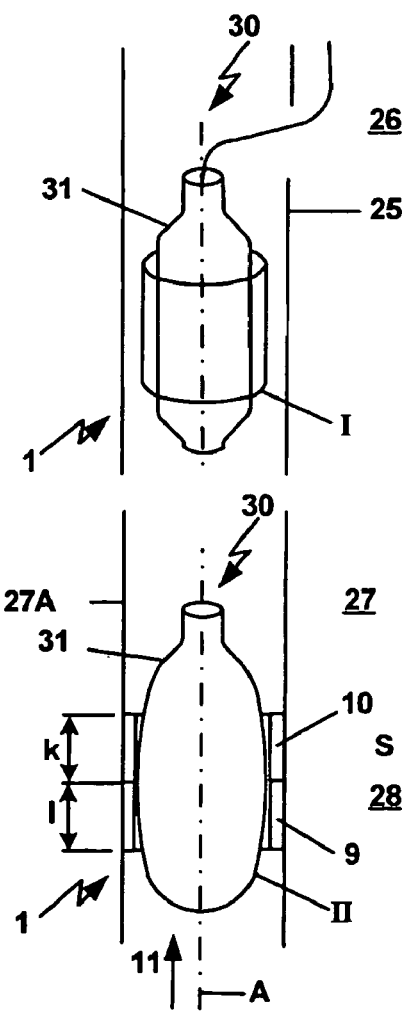
Fig. 4A
Fig. 4B

IMPLANT VALVE FOR IMPLANTATION IN A BLOOD VESSEL

CROSS-REFERENCE TO RELATED APPLICATION(S)

This application claims priority from both (1) Dutch Patent Application Serial No. NL 1014095 that was filed on Jan. 17, 2000 and (2) PCT International Application Number PCT/NL01/00027 that was filed on Jan. 16, 2001.

The invention relates to an implant valve for implantation in a blood vessel.

An implant valve according to the preamble of claim 1 is known from U.S. Pat. No. 5,851,232 and is applied for regulating the blood circulation through a vascular system, such as the human vascular system.

U.S. Pat. No. 5,851,232 describes a venous valve having a flexible tube with an expandable flexible casing integrated with the tube, which tube has an axially contiguous part forming an unsupported flexible tubular valve body.

The valve according to U.S. Pat. No. 5,851,232 has a relatively complex construction due to the integration of the casing in the wall of the flexible tube. In addition, the unsupported flexible tubular valve body does not always allow for proper opening and closing of the valve.

EP 0 850 607 discloses a heart valve having a casing cooperating with the outer wall of the flexible tube, while support means are provided which do not form part of the support.

U.S. Pat. No. 5,855,601 discloses a heart valve having a casing cooperating with the inner wall of a tube, but the tube is not provided with a second, axially contiguous part forming a flexible valve body.

The vascular system, in particular the venous vascular system in legs and arms, is, at certain locations, provided with bag-shaped valves, also called "cusps". The function of the valves is to impede the blood flowing against the direction of the blood circulation through the vascular system. In particular, this function is important in the period of relatively low blood pressure in the vascular system, occurring between systoles of the heart.

In some cases, however, the valves in the vessels of the vascular system do not close properly, so that blood can flow through the valves against the blood circulation. This problem especially occurs when the valves are damaged as a result of blood clots (thrombosis). Further, the closing action of introduce the implant valve into a vein at an easily accessible location, for instance, at the location of the groin, and to transport the implant valve with the aid of an inserter through the vein to a desired location, for instance at the location of the lower leg just under of above the knee, and there to fix the implant valve in the vein by expansion. An implant valve with an expandable support provided with bag-shaped valves and a method for percutaneously fitting such an implant valve in a vein are known from NL 1004827.

A drawback of the known implant valve is that it, in itself, increases the chance of clotting of blood or thrombosis considerably. In particular, the chance exists that in the flow direction, directly behind the bag-shaped valve body near the location where it abuts the wall of the vein, clotting of blood occurs through insufficient circulation. Further, the known valve body is provided with a relatively rough and irregular surface, which increases the chance of clotting through adhesion. Also, the flow resistance in the direction of the blood circulation is not optimally low.

Further, the known valve is difficult to manufacture because of its complex construction. In particular, the manufacture of the valve body from body specific material is a problem.

Additionally, because of the relatively complex construction of the implant valve, it has proved to be a problem to design it with a sufficiently small diameter to move it to body extremities such as forearms or lower legs.

The object of the invention is an implant valve which does not have the above-mentioned drawbacks. To that end, the invention provides an implant valve for implantation in a blood vessel, comprising a flexible tube and a hollow, substantially cylindrical support with a casing which is expandable in diameter from an initial position into an implantation position, the support extending over a part of the length of the tube substantially coaxially along the inner wall of the tube and the casing of the support cooperating with the inner wall of the tube such that, in the implantation position of the support, a first part of the tube can be formed to be a rigid shell which can be clamped substantially coaxially along the inner wall of a blood vessel, while a second, axially contiguous part of the tube can form a flexible, tubular valve body which can extend substantially free in the blood vessel.

Thus, it is achieved that the valve has a simple construction, so that it can be relatively easily manufactured with a small diameter. Further, the flexible tube of the valve can relatively easily be designed from body specific material. Additionally, the valve has a relatively low flow resistance, in particular when a substantially cylindrical flexible tube is applied, and when blood flows through it in the direction of the blood circulation from the rigid, tubular part, while circulation in the opposite direction through deformation of the tubular flexible valve body is effectively counteracted. Further, it is achieved that the chance of blood clotting as a result of the valve can be considerably reduced.

Further advantageous embodiments of the invention are described in the subclaims. The invention further relates to a method for implanting an implant valve and to a method for manufacturing an implant valve.

It is noted that in this context, for brevity's sake, an implant valve is also referred to as valve. The invention will be further elucidated on the basis of an exemplary embodiment, represented in a drawing.

In the drawing:

FIG. 3 shows a schematic cross section of a second embodiment of the implant valve;

FIGS. 4A and 4B show schematic representations of the implantation of the implant valve with the aid of a transport device.

It is noted that the Figures are only schematic representations of preferred embodiments of the invention. In the Figures, identical or corresponding parts are designated by the same reference numerals.

Figure 1B:
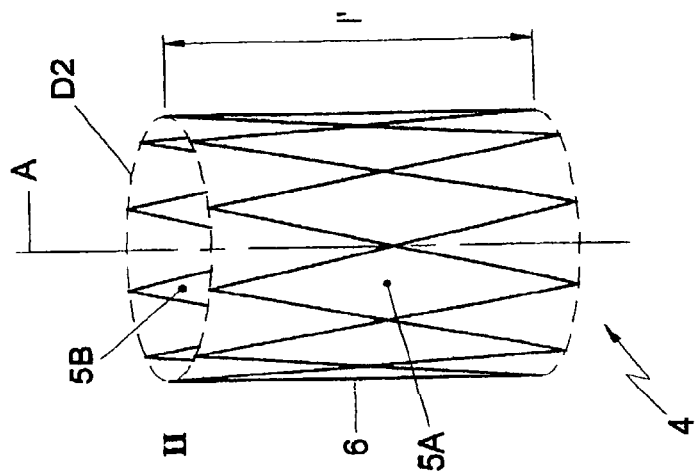
FIG. 1B shows a schematic perspective view of a support in implantation position.
Figure 1A:
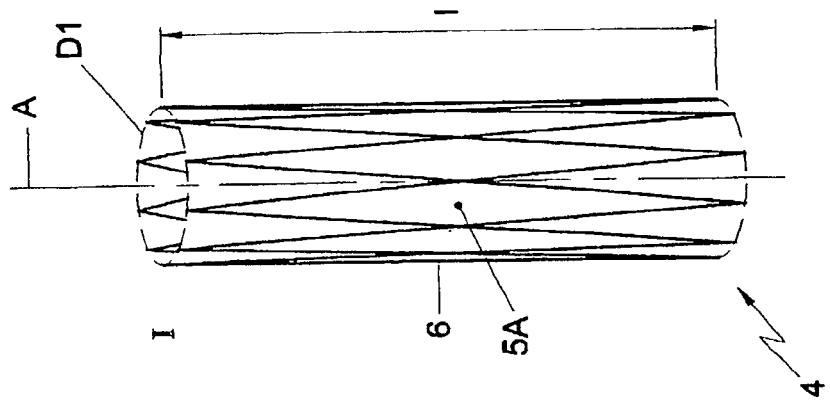
FIG. 1A shows a schematic perspective view of a support in initial position.
Figure 1:
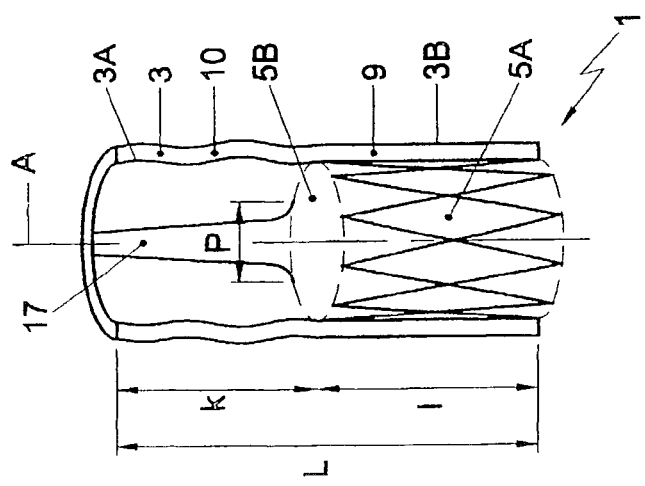
FIG. 1 shows a schematic, partly sectional perspective view of a first embodiment of the implant valve.
Figure 2A:
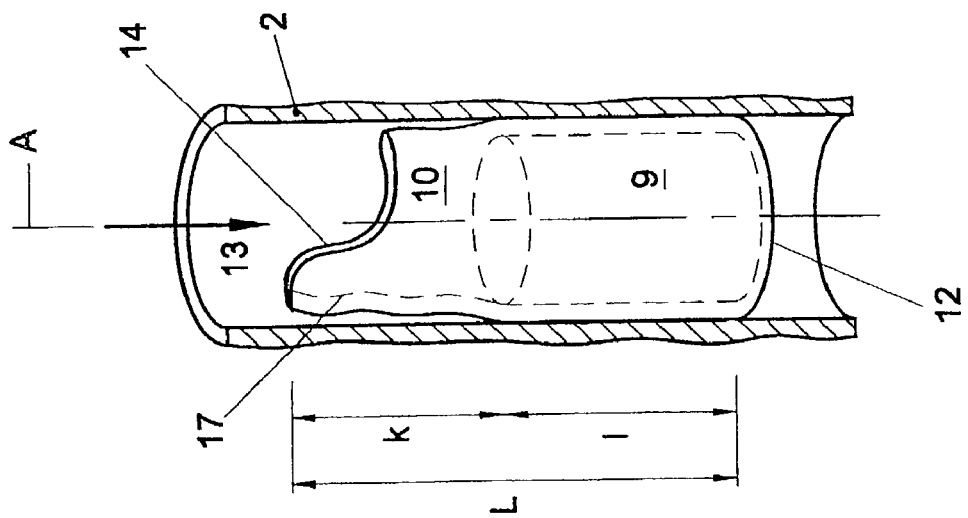
FIG. 2A shows a schematic perspective view of the implant valve of FIG. 1 in implanted condition during a systole of the muscle pump.

Referring to FIGS. 1 and 2, there is shown an implant valve 1 for implantation in a blood vessel 2. The implant valve 1 comprises a flexible tube 3 and a hollow, substantially cylindrical support 4. The tube 3 is manufactured from biocompatible material, preferably body specific material. The support 4 has a casing 5, expandable in diameter from an initial position I to an implantation position II. FIG. 1A shows the support 4 in the initial position I and FIG. 1B shows the support 4 in the implantation position II. From the initial position I, the support 4 expands over its entire length l in radial direction in relation to its longitudinal axis A, such that the diameter of the casing 5 of the support 4 increases from a first value D1 to a greater value D2. It is noted that, normally, the length l then decreases to a value l'.

The casing 5 of support 4 is preferably built up from an interlacement of two cylindrically interwoven, zigzagging, biocompatible metal wires 6. The interlacement can be designed to be pushed, with the aid of a balloon catheter, from the initial position I into the implantation position II (Balloon extendable type), but can also be designed from memory metal which, upon expansion, unfolds itself from the initial condition into the implantation condition II (Self expandable type). Such supports are usually referred to as "stents", and, since they are generally known, will not be further elucidated here.

The support 4 extends over a part l of the length L of the tube 3. The casing 5 of the support 4 is connected to the inner wall 3A of the tube 3, for instance in that the wires 6 of the casing 5 of the support 4 are sewn to the tube 3, such that the inner wall 3A, in the implantation position I, loosely envelops the outer casing surface 5A of the support 4. The outer surface 5A of the casing 5 cooperates with the inner wall 3A of the tube 3 such that, in the implantation position, the inner wall 3A is pulled taut by the outer surface 5A of the support to form a rigid shell 9. The rigid shell 9 extends over a first part l of the length L of the tube 3. A second part of the tube 3 contiguous thereto in axial direction A is not supported by the support 4 and forms a flexible, tubular valve body 10.

In implanted condition in a blood vessel 2, the rigid shell 9 extends substantially coaxially along the inner wall 2A of the blood vessel, and the outer wall 3B of the tube 3 is clamped by the support 4 in implantation position II, in a tubular shape, against the inner wall 2A of the blood vessel 2. The second part of the tube 3 contiguous thereto in axial direction forms a flexible, tubular valve body 10 extending over a part k of the length L of the tube, extending substantially clear in the blood vessel 2. In particular, the outer wall 3B of the tube 3 is then substantially clear of the inner wall 2A of the blood vessel 2.

In implanted condition, blood can pass in the direction of the arrow 11 in the direction of the blood circulation through the implant valve 1, for instance upon a systole of the muscle pump. The inflow opening 12 of the implant valve 1 coincides with the beginning of the rigid shell 9, so that the blood can flow easily into the implant valve 1. Subsequently, the flexible, tubular valve body 10, as a result of the flow of the blood in the direction of the arrow 11, is pulled taut, so that blood can flow through the implant valve 1, with little flow resistance in the direction of the arrow 11, to the exit outflow opening 14 of the valve.

The flexible tube 3 is preferably substantially cylindrical, or diverging so that an orifice can be achieved whose opening increases or is as constant as possible. In practice, with a cylindrical tube 3, the outflow opening 14 can be slightly smaller than the inflow opening 12.

Figure 2B:
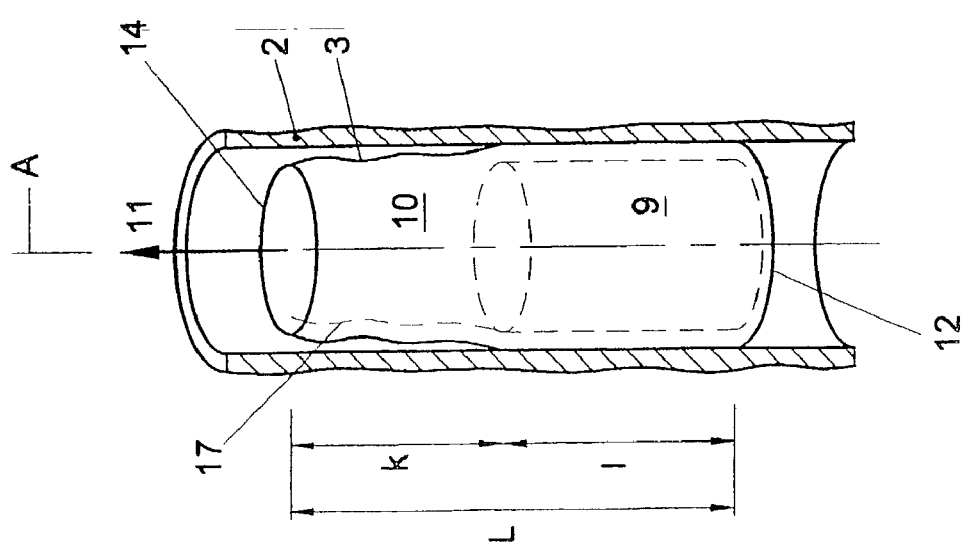
FIG. 2B shows the implant valve of FIG. 2A in the diastolic phase between two systoles of the muscle pump.

When, during a period between two systoles of the muscle pump, the blood tends to flow in the opposite direction of the blood circulation, i.e. in the direction of the arrow 13, for instance under the influence of gravity, the flexible, tubular valve body 10 will collapse (FIG. 2B). The flexible, tubular valve body 10 is insufficiently rigid to keep the outflow opening 14 open. Already under the influence of an initial flow against the blood circulation in the direction of the arrow 13, the flexible, tubular valve body 10 will collapse and cover the flow orifice of the rigid shell 9 as a valve and thus impede the flow through the valve body 1.

Upon a subsequent systole, the flexible, tubular valve body 10 will be stretched again as a result of a flow in the direction of the blood circulation. Since the flexible tubular valve body 10 in each case virtually abuts the inner wall of the blood vessel 2 to subsequently collapse, it is avoided that blood can reside between the tubular valve body 10 and the inner wall 2A of the blood vessel 2 for a long time.

Preferably, the ratio of the length of the part l to the part k is in the interval of 1:2 tot 2:1. Advantageously, the length of the part l is less than or equal to the length of the part k.

To prevent that the valve body 10, under the influence of a flow in the direction of the arrow 13, folds back into the passage of the rigid shell 9, and allows a renewed flow in the direction of the arrow 13, the support 4 can be provided with support means extending in the direction of the longitudinal axis A. The support means support the inner wall 3A along a part P of the circumference over at least a part of the length F of the second part k of the tube 3, corresponding to the flexible, tubular valve body 10. In the embodiment shown in FIGS. 1-2, the support means are designed as a finger-shaped extension 17 of the casing 5 of the support 4. Also, instead of one finger-shaped extension 17, for instance, two finger-shaped extensions 17, situated opposite each other can be provided, or three finger-shaped extensions 17 interspaced along the circumference of the casing 5.

Referring to FIG. 3, there is shown a second embodiment of the implant valve 1. In this embodiment, the tube 3 is folded double so that the inner wall 3A of the tube 3, from the outer surface 5A of the casing 5, while forming the flexible tubular valve body 10, extends along the inner surface 5B of the casing of the support 4. Thus, it is achieved that the support 4, along its inner casing 5B, can be smoothly covered, which facilitates the circulation through the valve and decreases the chance of blood clotting.

The ends 20, 21 of the tube 3 are connected to form a ring around the support. Hence, the tube 3 is connected around the support 4. By placing the connected outer ends 20, 21 of the tube 3 at the outer surface 5B of the casing 5, it is achieved that the ends 20, 21 of the implant valve 1, in implanted condition, are pushed against the inner wall 2A of the blood vessel 2 and no blood flows around them. Thus, the entire surface of the implant valve 1, around which, in implanted condition, blood flows, can be smooth, so that the flow resistance of the implant valve 1 is further reduced and the chance of blood clotting is further reduced.

In an advantageous manner, the implant valve is manufactured from a substantially cylindrical part of a vein. By turning the vein inside out, it can be achieved that the outer surface 3B of the tube 3 is formed by endothelial cells. In particular when the outer ends 20, 21 of the vein, turned-inside out, are connected in a ring-shape and the outer ends 20, 21 are situated at the outer surface 5B of the casing 5, as is described hereinabove, an implant valve 1 is obtained with a very low flow resistance in the direction of the blood stream and a very small chance of it causing blood clotting.

Preferably, the implant valve 1 is manufactured from a part of a body specific vein. For instance, from a patient, a substantially cylindrical part of a vein situated near the surface of the body, can be removed to be subsequently applied as a flexible tube 3 for an implant valve 1 which is implanted in a deeper vein. Thus, from a patient suffering from thrombosis, a part of a vein situated near the surface of the lower leg can be removed to be subsequently applied as a flexible tube in an implant valve which is implanted in a deeper vein in the lower leg of that patient.

The implant valve 1 can be manufactured by positioning the support 4 with its inner casing 5B around the outer wall 3B of the tube-shaped part 3, and turning the tube-shaped part 3 inside out by folding the ends 20, 21 of the tube part along the outer casing 5A of the support 4, and connecting the ends to each other, thus forming a flexible, tubular valve body 10 axially contiguous to the support 4. The ends 20, 21 of the tube can be connected to each other in a surgical manner known per se, for instance by stitches 18. In such a manner, the inner surface 3A of the tube 3, i.e. the original outer surface of the vein, can be connected to the outer and inner surface 5A, 5B of the casing 5, respectively, such that the tube 3, in implantation position II of the support 4, is positioned tightly along the outer surface 5A of the casing 5. In this manner, it can be achieved that only the layer of the tubular part of the vein covered in endothelium can contact the blood, while the support and any support parts 17 connected thereto are covered and protected from the blood.

The implant valve 1 can be implanted by positioning the implant valve 1 with the support 4 in initial position I in a blood vessel and transporting it, with the aid of a transport device, through the vein to an implantation site (FIGS. 4A and 4B). An example of thus is the percutaneous or minimally invasive insertion of the implant vale in a vein at the location of the groin 26 of a person and, after possible removal of badly functioning valves present in the vein 26, transporting the implant valve 1 through the vein 26 to apart of that vein which forms the location of implantation 28, situated just below or over the knee 27. The implant valve 1 can then be fixed by bringing support 4 into the implantation position II, so that a first part of the tube is clamped as a rigid shell 9 substantially coaxially along the inner wall 27A of the vein 27, while a second part of the tube 3, contiguous in the direction of the axis A, forms a flexible, tubular valve body, extending substantially clear in the vein. The flexible, tubular vale body 10 is then, for instance, viewed from the groin 26, situated before the rigid shell-shaped part 9, so that a downward flow through the valve body 10 against the blood circulation, resulting from gravity, is avoided, while an upward flow as a result of the systole of the heart in the direction of the blood circulation is obstructed as little as possible.

Preferably, as a transport device, a balloon catheter 30 can be used. The implant valve, with the support 4 in initial position I, is then fitted coaxially around the balloon 31 of the balloon catheter 30. The implant valve can be fixed at the implantation location 28 by expanding the balloon 3, thus bringing the support 4 into the implantation position II. After shrinkage of the balloon 3, the balloon catheter 30 can subsequently, while leaving the implant valve 1 behind, be recovered. Balloon catheters and the manner of operation thereof are known to the skilled person and will not be further elucidated here.

It is also possible to use different types of transport devices. For instance, an implant valve can be equipped with a support of the "Self-expandable" type, in which the support is kept in the initial position by fitting the implant valve into a sleeve. The transport device can then be formed by a sleeve which, with the aid of a coaxial cable, can be inserted and where, by displacing the cables relative to each other, the implant valve can be pushed from the container, after which it expands itself.

It will be clear that the invention is not limited to the preferred embodiments discussed here, but that many variations are possible. In particular, the flexible tube and/or the support can be manufactured from biocompatible plastic material. Also, the support means, in particular the finger-shaped extensions, can be provided with a protective layer or can be made of a somewhat flexible design to reduce the chance of damage to the flexible tube during use and to increase durability of the implant valve.

Such variants are understood to fall within the scope of the invention as set forth in the following claims.

The invention claimed is:

1. An implant valve for implantation in a blood vessel, comprising:
    a flexible tube; and
    a hollow, substantially cylindrical support extending over a part of a length of the flexible tube substantially coaxially along a wall of the tube, the support comprising a casing that is expandable in diameter from an initial position to an implantation position having an expanded diameter that causes the tube to contact an inner wall of the blood vessel, wherein the casing when expanded to the implantation position comprises:
        a first portion that supports a first part of the tube to provide a shell for clamping substantially coaxially along the inner wall of the blood vessel; and
        a second portion that configures a second, axially contiguous part of the tube to provide a flexible, tubular valve body, which in use extends substantially clear of the inner wall of the blood vessel;
    wherein the support includes an axially extending finger-shaped extension configured to support at least a portion of an inner wall of the second part of the tube that forms the flexible, tubular valve body, and wherein the flexible, tubular valve body formed from the flexible tube by the second portion of the casing is configured to allow blood to pass through in a first direction and to collapse so as to restrict passage of blood in a second direction opposite the first direction.

2. The implant valve of claim 1, wherein the finger-shaped extension comprises two or three finger-shaped extensions interspaced along the circumference of the casing.

3. The implant valve of claim 1, wherein the tube is folded double so that the inner wall of the tube extends from an outer surface of the casing while forming the second part of the tube to an inner surface of the casing of the support.

4. The implant valve of claim 3, wherein ends of the tube are connected to form a ring around the support.

5. The implant valve of claim 4, wherein the connected ends of the tube are situated at the outer surface of the casing.

6. The implant valve of claim 5, wherein the tube is formed of part of a vein which has been turned inside out, such that an endothelium of the vein forms an outer surface of the tube.

7. A method for implanting an implant valve according to claim 1, wherein the implant valve, with the support in the initial position, is placed in a blood vessel and wherein the implant valve, with the aid of a transport device, is transported through the blood vessel to a location of implantation, wherein, subsequently, the diameter of the casing of the support is brought into the implantation position, so that the first part of the tube is clamped as the rigid shell, substantially coaxially along the inner wall of the blood vessel, and the second, axially contiguous part of the tube forms the flexible, tubular valve body extending substantially clear of the inner wall of the blood vessel.

8. A method for manufacturing an implant valve for implantation in a blood vessel according to claim 6, from a tubular part of a vein and the hollow, substantially cylindrical support with the casing expandable in diameter from the initial position to the implantation position, the method comprising:
  turning the part of the vein inside out; and
  connecting the ends of the tube to form the ring surrounding the support, wherein an original outer wall, while forming a flexible, tubular valve body, axially contiguous to the support, is connected to the inner surface and the outer surface of the casing.

* * * * *